(12) United States Patent
Carturan et al.

(10) Patent No.: US 7,229,808 B2
(45) Date of Patent: Jun. 12, 2007

(54) BIOREACTOR

(75) Inventors: Gianni Carturan, Luxembourg (LU); Roberto Dal Toso, Luxembourg (LU); Renzo Dal Monte, Luxembourg (LU)

(73) Assignee: Silbiotec Due S.A., Luxembourg (LU)

( * ) Notice: Subject to any disclaimer, the term of this patent is extended or adjusted under 35 U.S.C. 154(b) by 363 days.

(21) Appl. No.: 10/500,556

(22) PCT Filed: Jan. 18, 2002

(86) PCT No.: PCT/EP02/00619

§ 371 (c)(1),
(2), (4) Date: Jun. 30, 2004

(87) PCT Pub. No.: WO03/060113

PCT Pub. Date: Jul. 24, 2003

(65) Prior Publication Data

US 2005/0084944 A1 Apr. 21, 2005

(51) Int. Cl.
*C12N 11/04* (2006.01)
(52) U.S. Cl. ............ 435/182; 435/176; 435/382; 435/395; 424/93.7
(58) Field of Classification Search ............ 435/182, 435/176, 382, 395
See application file for complete search history.

(56) References Cited

U.S. PATENT DOCUMENTS 6,214,593 B1 * 4/2001 Carturan et al. ............ 435/176

FOREIGN PATENT DOCUMENTS

WO WO 96/36703 11/1996
WO WO 97/45537 12/1997

OTHER PUBLICATIONS

Armanini et al., "SiO2 Entrapment of Animal Cells. Part 2: Protein Diffusion Through Collagen Membranes Coated With sol-gel SiO2." J. Mater. Chem., vol. 9, pp. 3057-3060 (1999).

* cited by examiner

Primary Examiner—Herbert J. Lilling
(74) Attorney, Agent, or Firm—Dickstein Shapiro LLP

(57) ABSTRACT

The present invention relates to a process for producing a bioreactor using viable immobilized biological material and to the bioreactor itself.

More particularly, the present invention relates to a process for producing a siliceous layer capable of biomass immobilization and selectively cutting off macromolecules having a molecular weight higher than a selected threshold, comprising the steps of:

a) supplying a gas flow of a gas carrier saturated by a mixture of silicon alkoxides selected from the group comprising (1)$Si(OR)_4$, (2)$SiH(OR)_3$, (3)$R'Si(OR)_3$ and (4)$R'SiH(OR)_2$ wherein R and R', equal or different each other, are alkyl and/or aryl groups, wherein said gas flow is prepared by bubbling the gas carrier into a liquid mixture of said alkoxides in the ratio of (1)40–85/(2)0–60/(3)0–60/(4) 0–60 (% v/v), preferably in the ratio of (1)40–85/(2)0–50/(3)0–50/(4)0–50 (% v/v), more preferably in the ratio of (1)50–80/(2)0–20/(3)5–30/(4)5–30 (% v/v), at a temperature of from 20 to 180° C., preferably of from 20 to 100° C., and b) exposing a support comprising a biomass to the gas flow of step a), wherein said selected threshold of molecular weight is chosen in the range of between 10,000 Dalton and 150,000 Dalton and wherein the ratio between the (1), (2), (3) and (4) Si derivatives in step a) is chosen as a function of the molecular weight of the macromolecules to be cut off.

19 Claims, 5 Drawing Sheets

BIOREACTOR

FIELD OF THE INVENTION

The present invention relates to a bioreactor.

In particular, the present invention relates to a bioreactor using viable immobilized biological material.

More particularly, the present invention relates to a bioreactor comprising a siliceous layer capable of immobilizing the above viable biological material, in the presence or not of scaffolding materials and matrices.

BACKGROUND ART

It is known that the immobilization or entrapment of biological material may be obtained by a siliceous layer deposited on the surface of a matrix holding a dispersion of said biological material such as, for example, enzymes, bacteria, yeast, plant or animal cells, hereafter named "biomass".

Such siliceous layer has to possess the following features:
a) immobilize the biomass preventing the release of the biomass from the matrix into the liquid medium of the bioreactor,
b) maintain the viability of the biomass allowing the controlled and defined transport between the immobilized phase and a culture medium, and
c) be biocompatible, so that body organs or fluids of living animals tolerate the contact with the immobilized biomass.

It is known a process for immobilizing a biomass by a sol-gel process, performed in solution starting from metal or silicon alkoxides in liquid phase.

However, the above process has several drawbacks such as, for example,:
a) it produces alcohols which are toxic in a number of biological systems,
b) the pH requirements may be unsuitable for living cells or may promote the denaturation of some bioactive enzymes,
c) the required stirring operations may be detrimental for cell lines sensitive to fluid-mechanical stresses,
d) some experimental procedures are incompatible with the required sterile environment, and
e) it is not applicable to biomasses requiring a definite structural organization to avoid loss of function.

In order to overcome the above problems, it has been suggested to immobilize the entrapped biomass within the matrix by means of a process which implies use of a gas medium carrying silicon alkoxides.

In particular, U.S. Pat. No. 5,998,162 describes plant cells immobilized in a siliceous layer obtained on the cell surface by reaction with gaseous silicon alkoxides. The immobilized cells are not released in solution over a period of six months and maintain their viability while producing secondary metabolites. Immobilized cells are used for pharmaceutical applications.

WO 97/45537 describes animal cells entrapped by a siliceous layer directly deposited on the cell surface by reaction with gaseous silicon alkoxides. The process is not toxic and viable cells are not leached by the medium and do not proliferate with medium invasion. Entrapped cells are used for bioartificial organs and for desired products.

However, it has been observed that, in some cases, the direct deposition of the siliceous layer on the cell surface reduces the effectiveness and function and that the body organs and/or the fluid of living animals were contaminated and the vitality of the viable biomass was quenched.

SUMMARY OF THE INVENTION

The inventors of the present invention have studied the above phenomena and have found that the effectiveness and function, in some cases require free contacts among biomass components in a gel matrix and that the contamination was due to pathogen agents derived from the biomass, while the loss of viability of the biomass was due to antibodies of the fluid of host living organisms.

Indeed, antibodies of living organisms recognize epitopes on the surface of foreign animal cells of the biomass and therefore tend to destroy them.

The problem underlying this invention, therefore, is that of providing an immobilization system for biomass which allows of preventing the above mentioned inconveniences.

Such a problem is solved according to the invention by a bioreactor and a process for obtaining it as recited in the appended claims.

Further studies carried out by the inventors of the present invention have pointed out, on one hand, that antibodies and pathogen agents have a molecular weight higher than 150,000 Da and on the other hand, the siliceous layer of the prior art has a porosity that is unable to keep completely or exclude the above molecules.

It is therefore a first object of the present invention to provide a process for producing a siliceous layer capable of biomass immobilization and selective cutting off of macromolecules having a molecular weight higher than a selected threshold, comprising the steps of
a) supplying a gas flow of a gas carrier saturated by a mixture of silicon alkoxides selected from the group comprising (1) $Si(OR)_4$, (2) $SiH(OR)_3$, (3) $R'Si(OR)_3$ and (4) $R'SiH(OR)_2$ wherein R and R', equal or different each other, are alkyl and/or aryl groups, wherein said gas flow is prepared by bubbling the gas carrier into a liquid mixture of said alkoxides in the ratio of (1)40–85/(2)0–60/(3)0–60/(4)0–60 (% v/v), preferably in the ratio of (1)40–85/(2)0–50/(3)0–50/(4)0–50 (% v/v), more preferably in the ratio of (1)50–80/(2)0–20/(3)5–30/(4)5–30 (% v/v), at a temperature of from 20 to 180° C., and
b) exposing for a predetermined period a support comprising a biomass to the gas flow of step a),
wherein said threshold of molecular weight is chosen inside the range of between 10000 Dalton and 150000 Dalton and the ratio between the (1), (2), (3) and (4) Si derivatives in step a) is chosen as a function of the molecular weight of the macromolecules to be cut off.

The molecular weight of the macromolecules to be cut off will be selected on a case by case basis, in view of the particular application to which the bioreactor is destined.

For example, a cut off of macromolecules having a molecular weight higher than 150.000 Dalton allows the antibodies derived from the fluid of host living organisms and the pathogens derived from the biomass to be excluded from moving through the siliceous mesh, thus preventing reciprocal damage of body fluid and biomass. A cut off threshold of 70.000 Dalton stops also complement system's components—such as C1s (90 kD), C1qINH (80 kD), C3bINA (80 kD),C9 (80 kD) and C3PA (80 kD)—from passing the siliceous membrane. This prevents a non-antibody triggered activation of the complement to take place. On the other hand, the 70 kD cut off is sufficiently large to allow high molecular weight substances to diffuse from the biomass to the body fluid. Such substances may be for example the molecules of the extracellular matrix such as collagen, glycosaminoglycanes or fibronectin, which are essential for biocompatibility in implant applications. Conversely, a cut off threshold of 90 kD is less selective in stopping complement system's components, but allows a larger amount of substances to be exchanged.

Generally, it can be said that a siliceous membrane with a cut off threshold of 130 kD to 150 kD can be applied in the case of bioreactor of industrial scale, where the secretion and diffusion of high molecular weight molecules produced by the biomass to the culture medium should be maximally enhanced. On the contrary, a cut off threshold of 10 kD may be used, again in the bioreactor of industrial type, when low molecular weight molecules are to be produced by the biomass and isolated from the culture medium.

The ability of the siliceous layer of the present invention to cut off macromolecules with a selected threshold of molecular weight depends on the composition of the mixture of Si derivatives in step a), as will be described herein below.

As a general guidance, the presence in the Si derivative of alkoxy groups facilitates cross-linking formation and thus reduces the size of the pores in the formed siliceous membrane. The introduction, in the mixture, of a relatively small amount of a Si derivative with less alkoxy groups per silicon atom (such as $R'Si(OR)_3$ or $R'SiH(OR)_2$) has the effect of enlarging the membrane's mesh.

In particular, a binary mixture (A) of $Si(OR)_4$ and $R'SiH(OR)_2$ in a ratio of between 75:25 and 80:20 allows the formation of a siliceous membrane having a cut off of about 90 kD. By adding to such a mixture, in replacement of same amount of $Si(OR)_4$, an amount of $R'Si(OR)_3$ up to about 10% v/v—thus providing a mixture (B) $Si(OR)_4/R'SiH(OR)_2/R'Si(OR)_3$ in a ratio of 65–78%/20–25%/1–10%—a siliceous membrane with an increasing cut off up to 150 kD is obtained.

When $R'Si(OR)_3$ is further added to the Si derivatives mixture up to a content of about 20% v/v, always in replacement of same amounts of $Si(OR)_4$, the cut off threshold of the membrane gradually decreases to 10 kD. This configuration corresponds to a mixture (C) $Si(OR)_4/R'SiH(OR)_2/R'Si(OR)_3$ in a ratio of 53–70%/20–25%/10–22%. Without being bound by any theory, the mentioned effect is probably due to the increasing hydrophobicity and to the hindrance caused by the higher amount of alkyl groups (R' groups) which tend to obstruct the pores.

From the above discussion it appears clearly that the same cut off threshold in the range of between 90 kD and 150 kD may be obtained for example by reaction of either a ternary mixture (B) or a ternary mixture (C) (but with $R'Si(OR)_3$ in amounts not higher than 10%) in the appropriate composition, as depicted above. In addition, a cut off value of about 90 kD may also be obtained by a binary mixture (A), while a cut off threshold of between 10 kD and 90 kD is obtainable for example by reaction of mixture (C) having the $R'SI(OR)_3$ component in amounts above 10% v/v.

Preferably, R is ethyl or methyl and R' is methyl.

Typically, the gas carrier of step a) is air.

Preferably, the total gas flow of step a) is of from 0.05 to 10 L/min, for exposing periods corresponding to from 1 to 100 mL of total gas per square centimeter of exposed surface.

Preferably, the saturation temperature in step a) is of from 20 to 100° C.

Typically, the support of step b) is a matrix which adheres to a scaffolding material.

In another embodiment of the present invention, the support of step b) is a matrix in form of microspheres which adhere to the scaffolding material. Preferably such microspheres have a diameter of from 0.1 to 1.0 mm.

In further embodiment of the present invention, the support of step b) is a matrix in form of microspheres, of a preferred diameter of from 0.1 to 1 mm, without the scaffolding material.

In another embodiment of the present invention, step a) is carried out on a biomass supported on a scaffolding material without a matrix.

Typical examples of matrix are gels of collagen, agar, dextranes, peptones, alginates, carrageenan and colloids. Such a matrix may further contain radio-opaque materials, such as barium salts, and/or promoters for NMR imaging detection such as magnetic particles and NMR shift reagents.

Typical examples of scaffolding material are porous paper sheet, glass fibres, fabrics, textile fibres, porous ceramic, glass bodies, natural sponges and foam organic polymers. Particularly preferred scaffolding materials are natural sponges.

Preferably, the siliceous layer of the present invention has a thickness of from 0.01 to 10 μm, even more preferably of from 0.05 to 0.3 μm.

Preferably, the siliceous layer of the present invention has a critical shear thinning stress higher than 10 Pa, even more preferably of from 12 to 20 Pa.

It is therefore an object of the present invention to provide a bioreactor comprising a siliceous layer capable of biomass immobilization and selective cutting off macromolecules having a molecular weight higher than a selected threshold, said siliceous layer being obtainable by a mixture of silicon alkoxides selected from the group comprising (1)$Si(OR)_4$ (2)$SiH(OR)_3$, (3)$R'Si(OR)_3$ and (4)$R'SiH(OR)_2$ wherein R and R', equal or different each other, are alkyl and/or aryl groups, in a ratio of (1)40–85/(2)0–60/(3)0–60/(4)0–60 (% v/v), preferably in the ratio of (1)40–85/(2)0–50/(3)0–50/(4)0–50 (% v/v), more preferably in the ratio of (1)50–80/(2)0–20/(3)5–30/(4)5–30 (% v/v).

According to a particular aspect of the present invention the bioreactor uses immobilized enzymes. In this case, the said siliceous layer has to prevent the release of said enzymes into the liquid medium. In general, many biologically relevant enzymes have a molecular weight higher than 10,000 Da.

Therefore, the present invention provides a process for producing a siliceous layer capable of biomass immobilization and selective cutting off macromolecules having a molecular weight higher than a selected threshold, such a threshold being selected between 10,000 Da and 150000, comprising the steps of a) supplying a gas flow of a gas carrier saturated by a mixture of silicon alkoxides selected from the group comprising (1)$Si(OR)_4$, (2)$SiH(OR)_3$, (3)$R'Si(OR)_3$ and (4)$R'SiH(OR)_2$ wherein R and R', equal or different each other, are alkyl and/or aryl groups, wherein said gas flow is prepared by bubbling the gas carrier into a liquid mixture of said alkoxides in the ratio of (1)40–85/(2)0–60/(3)0–60/(4)0–60 (% v/v), preferably in the ratio of (1)40–85/(2)0–50/(3)0–50/(4)0–50 (% v/v), more preferably in the ratio of (1)50–80/(2)0–20/(3)5–30/(4)5–30 (% v/v), at a temperature of from 20 to 180° C., and exposing a support comprising a biomass to the gas flow of step a).

With the term "biomass", it is intended a biological material, either of animal or vegetal origin, that is capable of performing a function of biological type.

Typical examples of "functions of biological type" are the production of products suitable for treating diseases, the production of secondary metabolites and proteins such as enzymes, growth factors, cytokines and hormones.

Examples of such a biomass are animal and plant cells, either primary, stem and mutated cell lines, aggregates thereof, enzymes and microorganisms, all this biological material being used as such or modified by genetic engineering.

Examples of biomass capable of producing products suitable for treating a disease are Neuro 2A cell lines transfected with the proopiomelanocortin gene capable of producing beta-endorphin (as described in Saitoh, Y. et al. Cell Transplant. 1995, 4 Suppl 1:S13-7), for treating chronic pain, adrenal pheochromocytoma PC12 cells (ATCC CRL-1720) capable of producing dopamine, for treating Parkinson, submandibolar gland SCA-9 clone 15 (ATCC CRL-1734) capable of producing Nerve Growth Factor (NGF), for treating Alzheimer, human lymphoma H33HJ-JA1 (ATCC CRL-8163) capable of producing IL-2, for treating tumors, pituitary GH3 cells (ATCC CCL-82.1) capable of producing growth hormone, for treating hypophysial nanism, primary porcine hepatocytes capable of producing factor VIII, for treating hemophilia, primary porcine hepatocytes capable of producing factor XII, for treating Hageman signs, primary porcine kidney cells or Hep-G2 cells (as described in Mark A. Goldberg Proc. Natl. Acad. Sci. U.S.A 84:7972–7976, 1988) capable of producing erythropoietin, for treating anaemia, porcine pancreatic islets capable of producing insulin for treating insulin dependent diabetes mellitus type I, primary porcine hepatocytes for the use in extracorporeal bioartificial liver.

With the term "bioreactor", it is intended both a device of the type described in FIG. 1 of the present invention and a biological unit formed by a matrix containing a biomass immobilized by the siliceous layer according to the present invention.

Therefore, when the bioreactor of the present invention is a biological unit, it may be also of cell dimension.

The inventors of the present invention have further found that, when the support of the bioreactor according to the present invention is a matrix in form of microspheres containing the biomass, without the scaffolding material, said bioreactor may be injected directly in an organ of a patient in need thereof.

Typical example of organs wherein the bioreactor according to the present invention may be directly injected are dorsal roots of medullary, encephalon, Ganglions of the base, basal nucleous of Meynert, locations where tumors are surgically extirpated, portal vein, peritoneum and liver.

Therefore, it is a further object of the present invention the use of the bioreactor obtainable by the process described above for preparing an injectable pharmaceutical composition for performing functions of biological type.

Typically, the bioreactor of the present invention may be used as for the integration or substitution of a damaged organ as artificial organ.

Examples of biomass for the integration or substitution of damaged human organs are pancreatic cells such as Langherans islets for damaged pancreas, pig hepatocytes for damaged liver, cells derived from thyroid, parathyroid, cortex and medullary adrenal gland for damaged thyroid, parathyroid gland and adrenal gland.

The injectable pharmaceutical composition according to the present invention comprises an effective amount of the bioreactor in form of microspheres suspended in a conventional physiological solution.

The amount of bioreactor in form of microspheres in the injectable pharmaceutical composition according to the present invention may vary in a rather broad range depending on known factors such as, for example, the type of disease to be treated, the severity of the disease, the body weight of the patient, the number of dosage forms administered daily and the efficacy of the biomass chosen.

However, the optimum amount may be easy and routinely determined by the person skilled in the art.

Typically, the injectable pharmaceutical composition according to the present invention may contain the bioreactor in form of microspheres in an amount of from 100 to 50.000 microspheres/ml of physiological solution.

For example, when the bioreactor in form of microspheres according to the present invention comprises Langherans islets as biomass, the amount of microspheres, each comprising one or more islets, in the injectable pharmaceutical composition, is of from 2000 to 25000, preferably 10000 per kg of body weight.

The injectable pharmaceutical composition according to the present invention can be prepared according to techniques which are known to the skilled in the art and comprise procedure such as mixing, solubilization and sterilization.

BRIEF DESCRIPTION OF THE DRAWINGS

Further characteristics and advantages of the present invention will become clear from the following description of a preferred embodiment, given by way of non-limiting example, with reference to the appended drawings, in which:

FIG. 3 is the molecular-weight distributions (from T1 to T5) of the proteins obtained from Hep-G2 cells immobilized by the siliceous layer, compared with those obtained from non immobilized cells according to Example 3a.

DETAILED DESCRIPTION OF THE INVENTION

Figures 1, 1A:
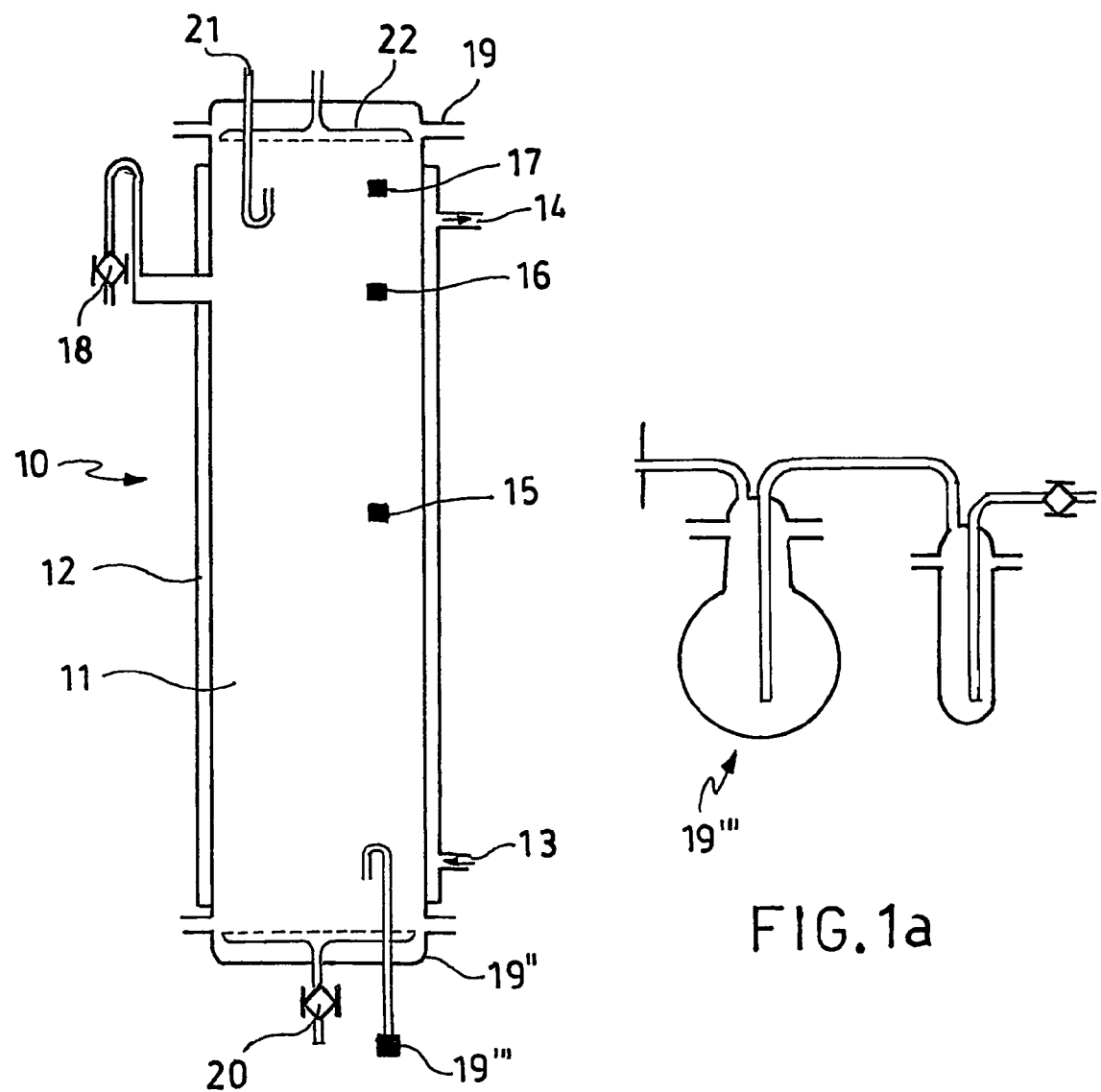
FIG. 1 is a schematic sectional view of a bioreactor (10) according to the present invention.
FIG. 1A is a schematic sectional view of the gas supplying removable device 19 ter connected to the mouth region 19 bis of the bioreactor 10 of FIG. 1.

FIG. 1 shows a bioreactor 10 according to the present invention comprising a vessel 11, a thermostated jacket 12 with inlet and outlet ports 13, 14, a pH and temperature sensors 15, 16, a dissolved oxygen probe 17, a service port 18, a removable top 19, a removable bottom 19 bis and a gas supplying device 19 ter.

In a preferred embodiment of the present invention the bioreactor 10 of FIG. 1 comprises a cylindrical vessel 11 made of non-toxic biocompatible material such as Pyrex™ or stainless steel. The vessel 11 is surrounded by the jacket 12 to provide temperature control by circulation of a heating fluid through inlet and outlet ports 13, 14. Heating/cooling fluid interior coils may alternatively be used. A pH probe 15, a temperature sensor 16, a dissolved oxygen probe 17 and a port 18 for feeding and sample collection during closed course working are coupled to vessel 11. Vessel 11 has removable top 19 and removable bottom 19 bis, which are hermetically sealed to the vessel by O-rings (not shown) and/or latches or bolts (not shown). The bioreactor 10 comprises a frame housing preferably made of steel, which keeps the vessel 11 in horizontal or vertical positions. Bioreactor 10, vessel 11, top 19 and bottom 19 bis are capable of being opened so that operators may access the interior for maintenance and manual work.

The cylindrical vessel 11 is loaded through suitable opening in the bottom 19 bis by the liquid suspension of biomass and a matrix compounds which are for examples collagen, agar, dextranes, peptones, alginates, carrageenan or analogous organic macromolecules in such concentration to produce a solid matrix gel below 40° C. Such a matrix may further contain radio-opaque materials, such as barium salts, and/or promoters for NMR imaging detection such as magnetic particles and NMR shift reagents.

Typically, the collagen concentration is of from 0.01 to 3% (w/v) and agar concentration is of from 0.5 to 3% (w/v).

Alternatively, the vessel 11 is filled with porous scaffolding material such as, for examples, glass fibers and fabrics, common fibers or fabrics, porous ceramic bodies, paper sheets, foam of organic synthetic or natural polymers and cellulose solids, all of which hold the biomass included in the above mentioned matrix compounds. These scaffolding materials may alternatively fill the vessel 11 and are there imbued by liquid suspension of the biomass and matrix compounds.

Alternatively, in the case of plant and yeast cells, liquid suspension of the biomass is used without matrix compounds.

The vessel 11 thus filled, is then exposed to a gas flow saturated by a mixture of gaseous silicon alkoxides according to the present invention. Said gas flow is supplied by the gas supplying device 19 ter removably connected to the bottom 19 bis.

The mixture of gaseous silicon alkoxides of the present invention produces a uniform and continuous siliceous layer on the surface of the matrix gel or on the surface of the biomass. The exposure time of the silicon alkoxide gaseous flux depends on the layer thickness (V. M. Sglavo et al. J. Mat. Science 34,3587 1999).

The siliceous layer thickness is a linear function of the exposition time up to 500 µg of silicon deposited per $cm^2$ of treated surface. The siliceous layer thus obtained provides an inorganic deposit attached to the matrix surface, independently of matrix chemical composition, geometry, shape, or presence of scaffolding materials.

When the siliceous layer produced according to the process of the present invention is formed, the mobile phase of the bioreactor may be circulated through the removable bottom 19 bis. This latter will be equipped with a gas spreader 20 supplying biomass oxygenation. The mobile phase may be used for feeding the biomass and for recovery of product compounds. Mobile phase circulation is provided by a feed pump (not shown) and moves in a closed circuit through the removable top 19.

The removable top 19 may comprise an outlet port 21 for the discharge of the gaseous flux saturated by silicon alkoxides and volatile byproducts of the siliceous layer formation.

Alternatively, the top 19 may comprise an outlet port for mobile phase circulation. In this embodiment, it may be connected to a line of extractors (not shown) providing liquid/liquid and/or gas/liquid continuous separation of desired products from the mobile phase. A reservoir connected to cover 19 may alternatively be used for substitution of the exhausted mobile phase and its storage for discontinuous working of the bioreactor.

Furthermore, the top 19 may comprise a spray nozzle 22 for producing droplets of the matrix solution. The spray nozzle 22 may be fed by the flux of silicon alkoxide gaseous mixture used to coat the droplets by the siliceous layer. In this embodiment, the removable bottom 19 bis may comprise the bubbling apparatus 19 ter used to saturate a non toxic gaseous flux by silicon alkoxides which invest falling droplets.

The present invention will be further described with reference to the Examples provided below merely by way of non restrictive illustrations.

EXAMPLE 1

Activity of Urease in 1% Agar and Immobilized by the Siliceous Layer

640 U of urease (purchased from Sigma, 99% purity) were mixed with 20 mL of 1% (w/w) agar (purchased from FMC, 99% purity) in water. The solution was poured into a glass Pyrex™ cylinder 30 mm in diameter and 300 mm in height in sterile conditions. The cylinder mouth and cover were closed and the cylinder was placed in a frame housing maintaining the vessel in horizontal position in a thermostated bath at 37° C. An external electrical motor imparted axial rotation to the cylinder at a rate of 5 rpm until the creation of a gel 0.7 mm thick on the internal wall of the cylinder. The mouth was connected to a gaseous flux saturated by a $CH_3SiH(OEt)_2$ and $Si(OEt)_4$ mixture obtained by bubbling the gaseous flux into a 25/75 volumetric liquid solution of those silicon alkoxides at 80° C. The carrier gas was air and the flux was 0.4 L/min. The flux was prolonged for 12 minutes. After completion of this operation, the cylinder was filled with a phosphatic buffer solution at pH=8.0 and stored at 37° C. for 15 hr with a 5 rpm rotation. After this time, samples of the buffer solution were collected; samples were also collected after 15 hr storage at pH=8.0 from another vessel containing the same urease load in the 0.7 mm thick agar gel not coated by the siliceous layer. The protein content in the samples was determined according to a modified Lowry's method (Peterson G. L., Anal. Biochem. 83:346 (1977)). Samples from the bioreactor not immobilized by the siliceous layer have a protein content corresponding to 100% urease leaching from the agar gel. Samples from the bioreactor with the siliceous immobilizing layer contain 0.7% of the protein content (100%=protein content measured in the case of non-immobilized samples). The enzymatic activity of urease was determined by monitoring the in-time decrease in the urea concentration in solutions starting from initial conditions of 5 µg of urea per 1U of free or immobilized urease. The urea concentration was determined with the diacethyl monoxime method (Ceriotti G. and Spadaro L., Clin. Chim. Acta 11:519 1965). Experiments were simultaneously carried out for solutions: 1. holding free urease, 2. holding urease in the agar not coated by the siliceous layer, and 3. holding urease in the agar coated by the siliceous layer. The activities of the enzyme in cases 1. and 2. were identical (same maximum rate and same Michaelis-Menten constant). In case 3., a definite improvement activity was observed (80% increase of maximum rate with same Michaelis-Menten constant).

EXAMPLE 2

Production of Lignanic Class Drugs from *Ruta graveolens* Cells Immobilized by the Siliceous Layer A sponge like layer of foam polyurethane 1 cm in thickness (density=0.1 g/mL) was cut into disks 3.0 cm in diameter. Disks were sterilized with steam at 120° C. and treated with a cell suspension culture of *Ruta graveolens* (generated from the sprout in 1995) holding 0.1 g of wet cell mass per mL. The medium was Gamborg's basal growth B5 solution supplemented with 3% (w/v) sucrose, 2.6 mg/L 2,4-dichlorophenoxyacetic acid, 0.30 mg/L kinetin, and 0.30 mg/L naphthalenacetic acid. The pH was adjusted to 5.7 with phosphatic acid. The disks were kept in the suspension in sterile conditions at 25° C. on a gyratory shaker operating at 100 rpm in a 12 hr period for 10 days. Disks were drawn out and hung to dry in a sterile hood at 30° C. for 2 hours. The average cell load was 0.3 g of wet mass per disk volume. 1000 disks joined by a metal yarn were introduced into a Pyrex™ cylindrical glass bioreactor 10 L in volume (15 cm in diameter, 57 cm in height). The reactor was maintained in a vertical position and treated from the bottom mouth with dry air at 30° C. (flux=0.8 L/min.) for 1 hour, then with a 5 L/minute air flux saturated by a $CH_3SiH(OEt)_2$ and $Si(OEt)_4$ mixture obtained by bubbling the gaseous flux into a 30/70 volumetric mixture of those silicon alkoxides at 75° C. Gaseous flux treatment lasted for 80 min. Gas admission was changed from the bottom mouth to the top cover with a 2 minute frequency, acting on a 4-way tap which connected the top and bottom sides to the gas flux entry and discharge. The reactor was immediately filled with the above described medium, which was changed after 30 minutes. Retained cell viability was determined by MTT (Mossman T. J. Immunol, Methods 65:55 (1983)) and was 92% with respect to viability measured before immobilization.

Figure 2:
FIG. 2 is a photo-micrograph of *Ruta graveolens* cells supported on foam polyurethane and coated by the siliceous coating according to Example 2.

The micrograph of FIG. 2 shows details of the siliceous layer immobilized cells on the polyurethane scaffolding material.

Temperature was maintained at 23° C. by circulation of thermostated water through a jacket surrounding the reactor. Circulation of the medium was provided by an external peristaltic pump operating with a delivery capacity of 5 L/hr. The liquid was passed through 4 liquid/liquid extractors; the preferred extraction liquid was a chloro solvent. The bottom mouth region was equipped with a gas spreader which provided an air flux of 10 L/hr. This flux was carried to the top cover and washed by bubbling into a phosphatic buffer at pH 7.2. The production of lignanic class drugs was observed in the chloro solvent used for liquid extraction and in the water solution used for washing discharged gas. Lignanic products were recovered by extraction with butanol-ethylacetate and separated by chromatography on Sephadex and by HPLC (Jasco Model PU 1580) using as solvent chloroform/methanol in a 9/1 volumetric ratio. The total product mass was 160 mg per day. Identification of lignanic products was made by FAB Mass Spectrometry. Identified products were Podophillotoxin, Diphyllin and Justicidin-A as major components, representing 80% of the total mass. Reactor productivity was maintained for 20 weeks upon 5 day frequency additions of sucrose to restore its concentration to 3% (w/v). Cell mortality appeared after 16 weeks and total mortality was observed after 20 weeks from siliceous layer immobilization.

EXAMPLE 3

Figure 3:
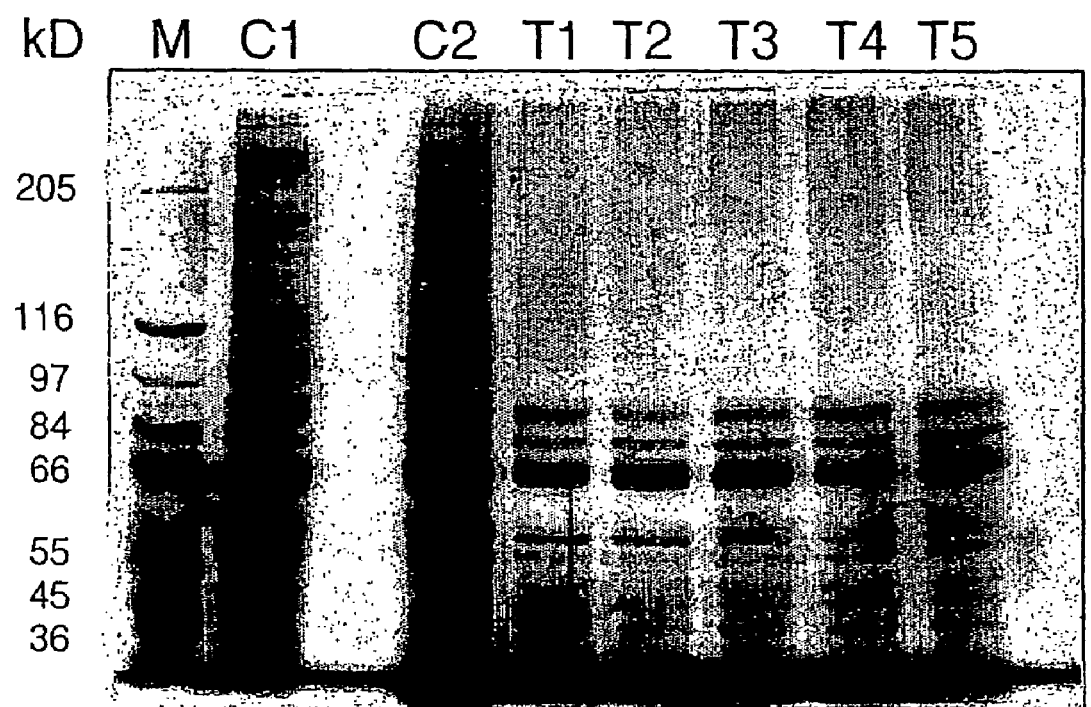

Molecular Cut-Off of Siliceous Layers Obtained from Different Mixtures of Silicon Alkoxides a) Hep-G2 cells were cultivated over a collagen layer deposited on Petri dishes 6 cm in diameter. The collagen matrix was obtained by heating a 0.1% (w/v) collagen solution at 37° C. The medium was Dulbecco's Modified Eagle's Medium supplemented with 10% of Fetal Bovine Serum. After cellular confluence to monolayer morphology, cells were coated with a 50 μm layer of collagen solution 0.1% (w/v). After consolidation, cell viability was 96%, as determined by Trypan blue exclusion. Samples were treated with medium and stored at 37° C. for 24 hours in a humidified atmosphere of 95% air and 5% $CO_2$. The medium was removed and 8 Petri dishes were mounted in a Pyrex™ glass cylinder 70 mm in diameter and 25 cm in height. A metal frame left 1.5 cm height space between dishes. Siliceous layer deposition was made according to Example 1 (temperature in cylinder=30° C., exposure time=8 minutes, 8 Petri dishes). After reaction, samples were immediately covered by the specified medium, which was replaced after 3 hours. The tiazolyl blue MTT assay for cell viability indicated 95% cell viability. 18 hours after siliceous layer coating, the biomass was subjected to lysis by reaction with a solution of Tris-HCl 50 mM (purchased from Sigma) at pH=8.0, $NaN_3$ 0.02% (w/v), and aprotinin 1 μg/mL (purchased from Sigma). After 24 hours, the solution was analyzed by the SDS-polyacrylamide gel separation procedure (Sambrook J. et al. "Molecular Cloning: a laboratory manual" Cold Spring Harbour Laboratory Press 1989). Samples were denatured at 100° C. for 3 minutes in 1×SDS gel loading buffer (50 mM Tris-HCl, pH=6.8, 100 mM Dithiotreitol, 2% w/v SDS, 0.1% (w/v) bromophenol blue, 10% (w/v) glycerol). Chromatographic runs were made on the mini PROTEAN II apparatus of Biorad (25 mM Tris, 250 mM glycine, 0.1% (w/v) SDS, pH=8.3 as mobile phase) operating at 180 V for 45 minutes. The gel was then incubated for 30 minutes 50% (v/v) methanol and 12% (v/v) acetic acid solution washed three times with 10% (v/v) ethanol plus 5% v/v acetic acid solution for 5 minutes, incubated with 3.4 mM $K_2Cr_2O_7$ and 3.2 mM $HNO_3$ solution, and then washed again three times with double distilled water. Samples were incubated with 12 mM $AgNO_3$ solution for 30 minutes. Protein band development resulted by treatment with 0.28 M $Na_2CO_3$ and 0.02% (w/v) formaldehyde solution and fixing in 1% (v/v) acetic acid solution. Referring to FIG. 3, protein distribution is illustrated as a function of the molecular weight of 5 samples coated with siliceous layer and subjected to lysis and 2 control samples (C1, C2) not coated by the siliceous layer but similarly subjected to lysis. Protein distributions obtained from coated samples and numbered T1 to T5 do not show traces of proteins with M. W. higher than 90,000 Da.

b) The same procedures of Example 3a were repeated in case of using, for the siliceous layer deposition, a 0.4 L/minute air flux saturated by a $CH_3SiH(OEt)_2$, $CH_3Si(OEt)_3$ and $Si(OEt)_4$ mixture obtained by bubbling the gaseous flux into Oct. 20, 1970 volumetric mixture of those alkoxides at 80° C. Protein distribution obtained from the coated samples subjected to lysis did not show traces of protein with M. W. higher than 150,000 Da.

c) The same procedures of Example 3a were repeated in case of saturation of the gaseous flux by a $CH_3SiH(OEt)_2$, $CH_3Si(OEt)_3$, and $Si(OEt)_4$ mixture in the volumetric ratio 20/20/60 at 75° C. Protein distribution obtained from the coated samples subjected to lysis do not show traces of proteins with M. W. higher than 10,000 Da.

EXAMPLE 4

Activity of *Bacillus polymyxa* and *Bacillus subtilis* in 1% agar and immobilized by the siliceous layer A stock of *B. polymyxa* was purchased from ATCC. A fraction of this culture was inoculated in 50 mL medium constituted of a solution of: yeast extract/casein/glucose/sucrose/NaCl/MgSO$_4$=2.5/2.5/8/2/1/0.5 g/L; the suspension was buffered at pH 7.3 and supplemented with 1 mL of $CaCl_2$ $2H_2O/FeSO_4 7H_2O/ZnSO_4 7H_2O/CuSO_4 5H_2O/MnSO_4 4H_2O$=1/1/1/0.5/4 g/L. The suspension was stored for 3 days at 27° C. 5 mL of the suspension were diluted with 1 L of medium constituted of said compounds in concentrations=2.5/2.5/18/2/1/0.5 g/L supplemented by tryptone (2 g/L) and ammonium sulfate (1 g/L) and buffered at pH 7.3. The obtained suspension was stored at 27° C. for 5 days under stirring. Agar was added to this suspension up to a 1% (w/v) concentration. 30 L of the suspension were poured into a stainless steel cylinder 20 cm in diameter and 100 cm in height, filled with 5000 disks of glass wool, 35 mm in diameter and 10 mm in height, obtained from a texture with density=0,2 g/mL. These disks were randomly arranged in the cylinder. The suspension was set aside for 30 minutes and then spurted out of the cylinder. The cylinder was placed in a frame housing maintaining the horizontal position of the vessel and under rotation at 5 rpm. The disks were here treated with a gaseous flux of silicon alkoxides, as described in Example 2. Treatment lasted for 6 hours. The vessel in the vertical position was filled with the above described medium. The viability of the biomass was checked by monitoring glucose consumption over a period of 8 weeks. Consumption of 1.3 g/L of glucose per day was constant and the original 18 g/L glucose concentration was restored by addition of glucose every two days.

Identical processing was used for immobilization of *B. subtilis*. In both cases, microscopic observations revealed the total absence of microorganisms released in the solution. Samples of the medium were collected for detecting the concentration of polymyxine and bacitracine, respectively. Antibiotic activity was tested by antibiograms on *Escherichia coli* as polymyxine sensitive stocks and on *Staphylococcus aureus* as bacitracine sensitive organism. Dilution of original samples with saline determined the trend of polymyxine and bacitracine production during the 8 weeks of observation.

EXAMPLE 5

Determination of Critical Shearing Stress of a 0.1 μm Thick Siliceous Layer on Collagen The critical shearing stress of the siliceous layer on collagen was determined by fluid mechanic experiments. A glass duct 120 cm long, 8 cm wide and 2 cm high was connected to a feed pump. Water was put into the duct, kept horizontal, starting from a minimum flow of 5 L/minute. A 0.1 mm thick collagen layer, consolidated from a 0,1% (w/v) solution, was deposited on the base of the duct, and flow was increased up to the removal of the layer. The corresponding critical flow gave a collagen critical shearing stress value of 0.5 Pa. The same experiment was carried out in the case of collagen coated by the siliceous layer, deposited according the procedure described in Example 2 using a 3 minute treatment. Critical shearing stress resulted to be 15 Pa.

EXAMPLE 6

Siliceous Layer Coating of Alginate Microspheres Containing Jurkat Cells

Alginate microspheres containing ($1 \times 10^7$ cells/mL; 2,400 cells/microsphere) were produced by conventional air-jet extrusion (Lim F. and Sun A. M. Science, 210:908 (1980). The alginate solution (1.5% w/V Na- alginate in 0.9% NaCl solution) containing Jurkat cells, a human lymphocyte cell line, was loaded into a sterile syringe barrel and the piston is guided by a uniformly driven pushing device. A sterile needle (0.3 mm internal diameter, 0.5 mm external diameter) was connected to the syringe and placed into a coaxial air-jet extrusion nozzle (0.65 mm diameter). Air-flux ranging from 0.4 L/minute to 0.8 L/minute was bubbled into a solution of $CH_3SiH(OEt)_2$ and $Si(OEt)_4$ (25/75 volumetric mixture) at 80° C.

The organosilane saturated air flux entered the air-jet extrusion nozzle, providing the siliceous coating and the dripping-off of the alginate drop from the needle tip. Microsphere diameter ranged from 0.2 mm to 0.8 mm depending on the gaseous flux. Microspheres, dropped into a 100 mM calcium chloride solution, were kept in this solution for 5 minutes and transferred into a cell culture medium (RPMI 1640). Cell viability was tested by the MTT assay and displayed more than 80% viability. The encapsulated Jurkat cells were stimulated with phorbol esters to secrete Interleukin 2 (IL-2), a lymphokine of 15,000 Da. After 24 hour of stimulation, IL-2 levels were determined in the surrounding culture medium (226 pg/ml) by a human IL-2 ELISA detection kit (Sigma Chemical Company, Saint Louis, Mo., USA, I-8273). The presence of the siliceous layer was demonstrated by osmotic lysis of microspheres in demineralized water.

Figure 4:
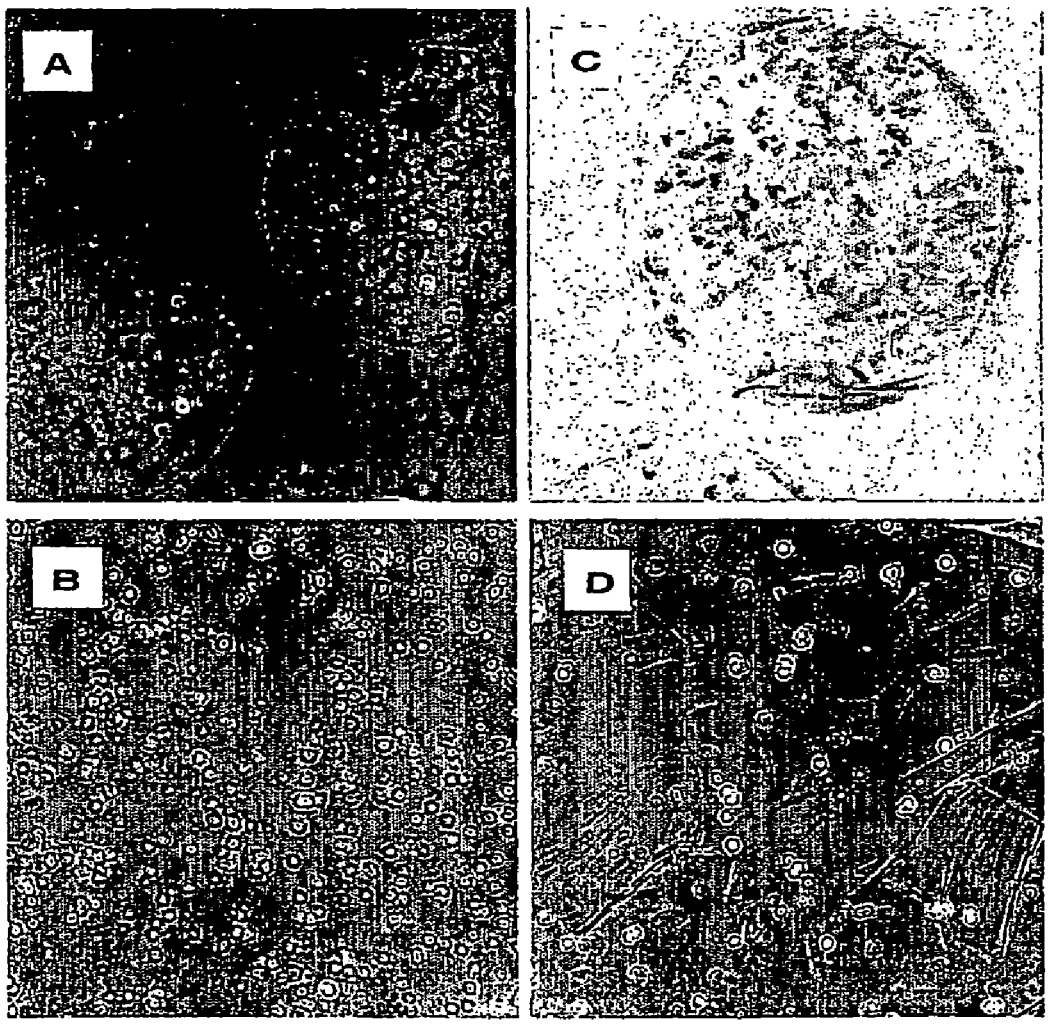
FIGS. 4A–4D are photo-micrographs of Jurkat cells in $Ca^{2+}$-alginate microspheres 500 μm in diameter. 4C shows the same microspheres coated by the siliceous layer. 4B refers to the same samples in the absence of the siliceous layer subjected to $Ca^{2+}$ removal. 4D shows the same samples coated by the siliceous layer and subjected to $Ca^{2+}$ removal (Example 6).

Dilution of calcium ions resulted in disruption of alginate microspheres so that free cells were liberated in solution (FIG. 4 B). Referring to FIG. 4 D, in the case of microspheres coated by the siliceous layer residual portions of the layer were observed together with free cells.

EXAMPLE 7

Langherans Islets Coating by the Siliceous Layer

Pancreatic islets were obtained from Lewis rats pancreas surgically isolated according to standard procedures. 200/300 islets were deposited on a 220 mesh net, suspended in a 1,5 mL Swining filter holder, and fluxed for 15 seconds with a 0.1 L/minute air saturated at 80° C. by $CH_3SiH(OEt)_2$ and $Si(OEt)_4$ (25/75 volumetric mixture).

Figure 5:
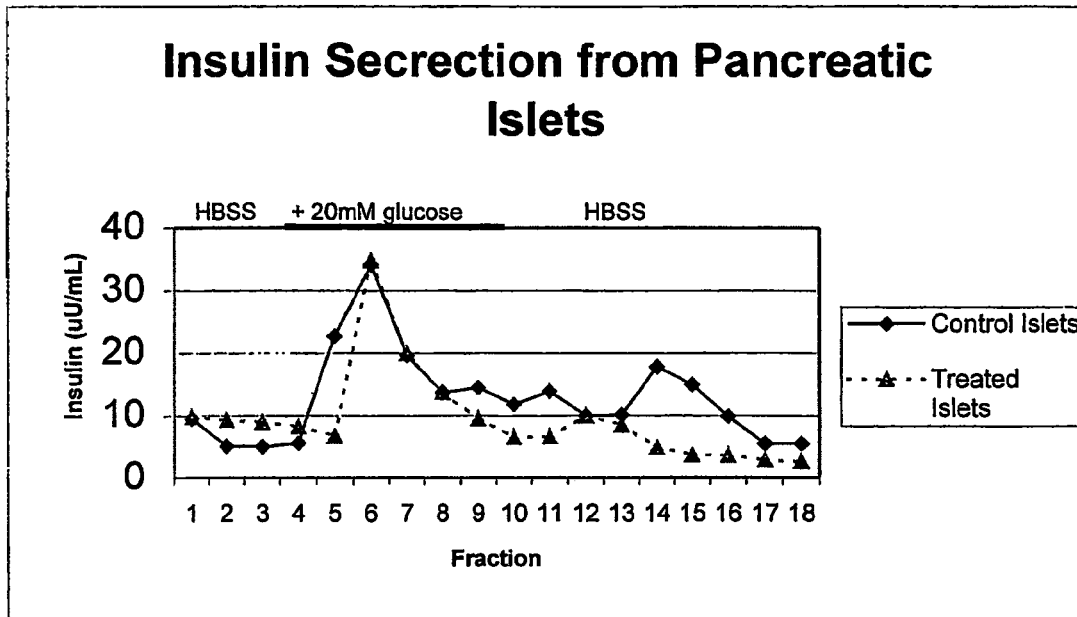
FIG. 5 Shows perfusion tests carried on control (square points) and silica coated (triangle points) Langherans Islets. The solid bar spans over the glucose challenge period.

Islets were transferred into a cell culture medium (DMEM) and incubated at 37° C. in a 5% $CO_2$ atmosphere for 24 hours. The islets were tested in vitro in a perfusion chamber with Hank's Balanced Salt Solution (HBSS, 0,5 ml/min) and a glucose challenge (20 mM in HBSS from fraction 4 to fraction 10, solid bar in FIG. 5) for detection of insulin secretion. Fractions were collected every 2 minutes.

Insulin content was determined in each fraction by a rat specific insulin antibody kit in an ELISA apparatus. Coated islets showed an insulin release trend imposable to the one obtained for control islets (see FIG. 5). Experiments were carried according to literature methods (Wang T. et al. Nature Biotechnology 15:358 (1997)).

Figure 6:
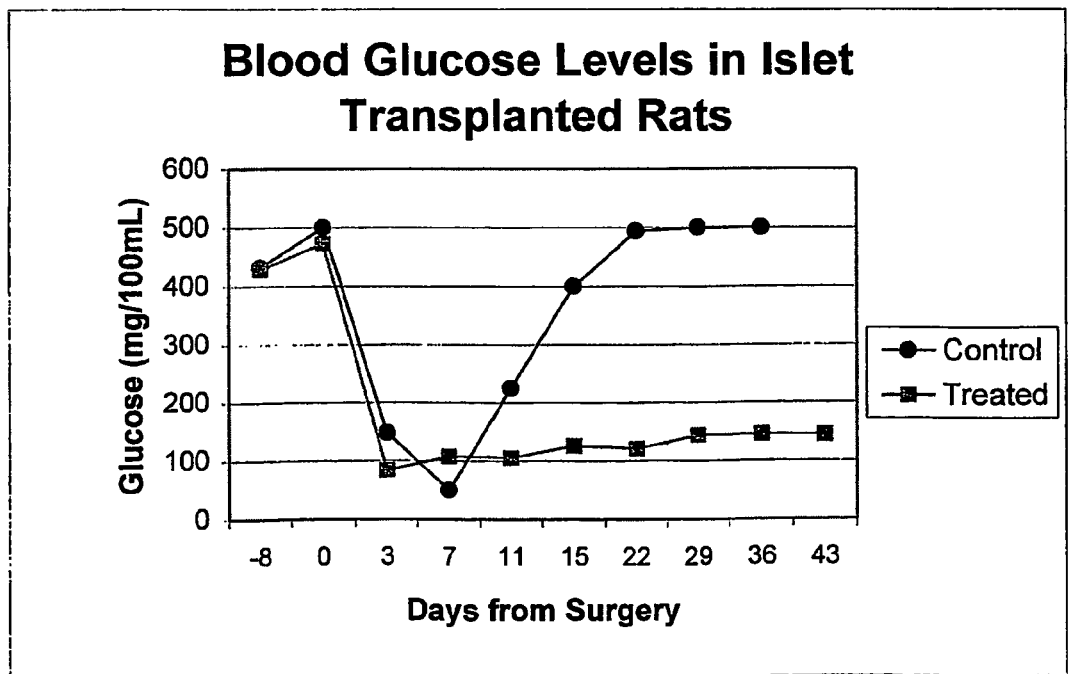
FIG. 6 Shows blood glucose levels in Sprague Dawley male rats transplanted with pancreatic Islets. Rats (6 per group) received approximately 600 Islets, either control (dots) coated with a siliceous layer (squares). Each point is the mean of six independent measurements, Standard Deviation was below 15% of mean for every point.

Pancreatic Langherans Islets deriving from Lewis rats (240 g of weight), both control and coated by a siliceous layer as previously described in this example, were utilized for allogenic surgical transplantation to male Sprague-Dawley rats (280 g of weight) made stably diabetic (glycemia over 300 mg/100 ml) by the intra peritoneal administration of streptozotocin (6 mg/100 g). Both donor and recipient rats were operated under anesthesia by halothane in a sterile operating room. Islets, approximately 600 per rat, were implanted between one kidney and its adrenal gland. Post-operative care included administration of one insulin injection to aid recovery of rats and transplanted Islets from surgical stress. For the determination of blood glucose levels, blood samples (100 µl) were collected from the tail of both control and transplanted rats once 8 days prior to surgery and, after, every 3 to 4 days for the first two weeks and then once every week. As shown in FIG. 6, the control animal group (n=6) transplanted with non coated Islets, regained diabetic blood glucose levels (300 mg/100 ml) 15 days following surgery, whereas animals (n=6) transplanted with Islets coated by the siliceous layer were still normoglycemic up to 43 days following implantation.

EXAMPLE 8

Biocompatibility of the Siliceous Layer a) Biocompatibility In Vitro (i) Complement activation. HepG2 cells were cultivated on Petri dishes according to the procedure described in Example 3a 0.5 mL of human blood plasma, in the absence of complement or with zymosan activation, were deposited on the collagen layer. Samples were stored for 30 minutes at 37° C. (Fushimi F., Nakayama M., Nishimura K., Hiyoshi T. Artificial Organs 22(10):821–826 (1998)). C5a levels were determined by ELISA analysis of the solution: the level measured for the sample treated with zymosan was considered 100% level. The same experiment was carried out with HepG2 cells in the collagen coated by the siliceous layer, prepared according to Example 3a (exposure time 6 minutes, 6 Petri dishes). The C5a complement concentration was 5% of the zymosan treated sample.

(ii) Kallicrein activity. HepG2 cells were cultivated on Petri dishes according to the procedure described in Example 3a 0.5 mL of bovine plasma solution (containing citrate and diluted from 3 to 5 volumes with 60 mL Tris-HCl) were deposited on the collagen layer. Samples were stored for 60 minutes at 4° C. The supernatant liquid was treated with z-Fe-Arg-7-amino-4-methyl-coumarin which detected the conversion of prekallicrein to kallicrein operated by factor XII (Fushimi F., Nakayama M., Nishimura K., Hiyoshi T. Artificial Organs 22(10):821–826(1998)). The kallicrein level resulting from this analysis was considered 100%. The same experiment was carried out with HepG2 cells in collagen coated by the siliceous layer, prepared according to Example 8a(i). The kallicrein level was 3% of the non coated sample.

(iii) Platelet adhesion. Experiments of platelet adhesion on the siliceous layer deposited on the collagen matrix were carried out according to Example 8a(i) (Fushimi F., Nakayama M., Nishimura K., Hiyoshi T. Artificial Organs 22(10):821–826 (1998)). Results indicated the total absence of platelet activation by the siliceous layer.

(iv) Red Blood Cell Hemolysis. Possible red blood cell lysis induced by contact with the siliceous layer, or by release of toxic substances from the layer, was evaluated according to reported procedures (Drabkin D. L., Austin J. H. J. Biol. Chem. 98:719 (1932)) by measuring the spectrophotometric concentration ($\lambda$=540 nm) of hemoglobin in blood samples stored in contact with the siliceous layer deposited on the collagen matrix according to Example 8a(i). No lysis was observed after 3 hr at 37° C.

b) Biocompatibility In Vivo.

Biocompatibility in vivo was assessed by the injection of both silica treated and normal collagen coated dextran microspheres (Cytodex, Pharmacia, approximately 100 µm in diameter) in the hind leg muscles of mice.

Groups of microspheres were laid on a 220 Mesh stainless steel net in a 30 mL cylindrical teflon reaction chamber with inlet and outlet ports on opposite sides of the net. The microspheres were treated with an air flux saturated as described in Example 2 for 30 minutes. Treated microspheres were then collected in 3 mL of sterile cell culture medium and concentrated by centrifugation (200×g for 5 minutes). Both treated and control microspheres were then resuspended in sterile phosphate buffered saline (pH 7.4) to a concentration of 6 million microspheres per milliliter of buffer. Three groups of 5 mice were injected by sterile syringes with 50 µL of a silica treated microsphere suspension, three groups of 5 control mice were similarly injected with a suspension of non treated microspheres; all animals were anesthetized during this operation. Mice were then sacrificed for autoptical observation and tissue collection at 2 weeks, 4 weeks and 12 weeks following injection. No signs of inflammation, pain or functional loss appeared to be present during the period of between microsphere injection and sacrifice in all groups. At the end of each test period, mice were sacrificed with excess anesthesia and the hind leg muscle collected for macroscopical inspection and histological analysis. No signs of infection, inflammatory processes, bleeding or fibrosis were macroscopically evident at the injection site in all animal groups. The subsequent microscopical observation of muscle tissue morphology of 5 µm thick histological slices following Geimsa staining, resulted in the absence of any sign of edema, protein extravasation, leukocyte cell infiltration and fibrotic scar tissue formation at the site of injection in treated animal groups, whereas in control animals there was evidence of fibrotic reaction in the tissue around the control uncoated microspheres.

The invention claimed is:

1. A process for producing a siliceous layer capable of biomass immobilization and selectively cutting off macromolecules having a molecular weight higher than a selected threshold, comprising the steps of:

a) supplying a gas flow of a gas carrier saturated by a mixture of (1) Si(OR)$_4$, (2) R'Si(OR)$_3$ and (3) R'SiH(OR)$_2$, wherein R and R', equal to or different from each other, are alkyl and/or aryl groups, wherein said gas flow is prepared by bubbling the gas carrier into a liquid mixture of (1), (2) and (3) in a ratio of either (1) 65–79%, (2) 1–10%, (3) 20–25% v/v or (1) 53–70%, (2) 10–22%, (3) 15–25% v/v, at a temperature of from 20 to 180° C., and b) exposing a support comprising a biomass to the gas flow of step a), wherein said selected threshold of molecular weight is chosen in the range of between 10,000 Dalton and 150,000 Dalton and wherein the ratio of (1), (2) and (3) in step a) is chosen as a function of the molecular weight of the macromolecules to be cut off.

2. A process according to claim 1, wherein R is ethyl or methyl and R' is methyl.

3. A process according to claim 1, wherein the ratio of (1), (2) and (3) in step a) is chosen in order to cut off macromolecules having a molecular weight higher than 10,000 Dalton.

4. A process according to claim 1, wherein the ratio of (1), (2) and (3) in step a) is chosen in order to cut off macromolecules having a molecular weight higher than 70,000 Dalton.

5. A process according to claim 1, wherein the ratio of (1), (2) and (3) in step a) is chosen in order to cut off macromolecules having a molecular weight higher than 90,000 Dalton.

6. A process according to claim 1, wherein the ratio of (1), (2) and (3) in step a) is chosen in order to cut off macromolecules having a molecular weight higher than 150,000 Dalton.

7. A process according to claim 1, wherein the content of $R'Si(OR)_3$ in the mixture of step a) is up to about 10% v/v and is added in replacement of a same amount of $Si(OR)_4$.

8. A process according to claim 1, wherein the content of $R'Si(OR)_3$ in the mixture of step a) is between about 10% v/v and about 20% v/v and is added in replacement of a same amount of $Si(OR)_4$.

9. A process according to claim 1, wherein the total gas flow of step a) is from 0.05 to 10 L/min for exposing times corresponding to from 1 to 100 mL of total gas per square centimeter of exposed surface.

10. A process according to claim 1, wherein the support of step b) is a matrix which adheres to a scaffolding material.

11. A process according to claim 1, wherein the support of step b) is a matrix in the form of microspheres having a diameter of from 0.05 to 1.0 mm.

12. A process according to claim 1, wherein the support of step b) is a matrix in the form of microspheres having a diameter of from 0.05 to 1.0 mm and wherein the matrix in the form of microspheres is without a scaffolding material.

13. A process according to claim 1, wherein the support of step b) is a scaffolding material without a matrix and the biomass is directly supported on said scaffolding material.

14. A process according to claim 1, wherein the siliceous layer has a thickness of from 0.01 to 10 μm.

15. A process according to claim 1, wherein the siliceous layer has a critical shear thinning stress higher than 10 Pa.

16. A process according to claim 1, wherein the carrier gas is air.

17. A process according to claim 1, wherein the gas flow is prepared at a temperature of from approximately 20° C. to approximately 100° C.

18. A process according to claim 14, wherein the siliceous layer has a thickness of from 0.05 to 0.3 μm.

19. A process according to claim 15, wherein the siliceous layer has a critical shear thinning stress of from 12 to 20 Pa.

* * * * *